United States Patent
Dalal et al.

(10) Patent No.: US 8,373,018 B2
(45) Date of Patent: Feb. 12, 2013

(54) PROCESS FOR GENERATING TRANSGENIC ANIMALS USING RECOMBINANT LENTIVIRUSES

(75) Inventors: Sorab N. Dalal, Maharashtra (IN); Lalit Sehgal, Maharashtra (IN); Nileema Khapare, Maharashtra (IN); Rahul Thorat, Maharashtra (IN)

(73) Assignees: Advanced Centre for Treatment, Research & Education in Cancer (ACTREC), Maharashtra (IN); Department of Biotechnology, New Delhi (IN)

( * ) Notice: Subject to any disclaimer, the term of this patent is extended or adjusted under 35 U.S.C. 154(b) by 0 days.

(21) Appl. No.: 13/004,382

(22) Filed: Jan. 11, 2011

(65) Prior Publication Data

US 2012/0096573 A1    Apr. 19, 2012

(30) Foreign Application Priority Data

Oct. 13, 2010   (IN) .......................... 2442/DEL/2010

(51) Int. Cl.
    *C12N 15/00*       (2006.01)

(52) U.S. Cl. ............................. 800/21; 800/22; 800/23
(58) Field of Classification Search ............ 800/21–23
    See application file for complete search history.

(56) References Cited

PUBLICATIONS

Kantsu-Shinohara et al. Biology of Reproduction 71:1202-1207, 2004.*
Hamra et al. PNAS 99(23):14931-14936, 2002.*
Naito et al. J Reprod Fert 113:137-143, 1998.*
Dhup et al., "Transgenesis via permanent integration of genes in repopulating spermatogonial cells in vivo", Nature Methods, Jul. 2008, pp. 601-603, vol. 5, No. 7.

* cited by examiner

*Primary Examiner* — Marcia S Noble
(74) *Attorney, Agent, or Firm* — The Webb Law Firm

(57) ABSTRACT

A process for generating transgenic animals using recombinant lentiviruses. The process comprises injecting recombinant lentiviruses into the interstituim of the testis of a male to produce mature spermatozoa within a few days. The male with transgene expressing lentivirus is mated with a female, forming a progeny carrying the transgene.

6 Claims, 4 Drawing Sheets

Figure 1:
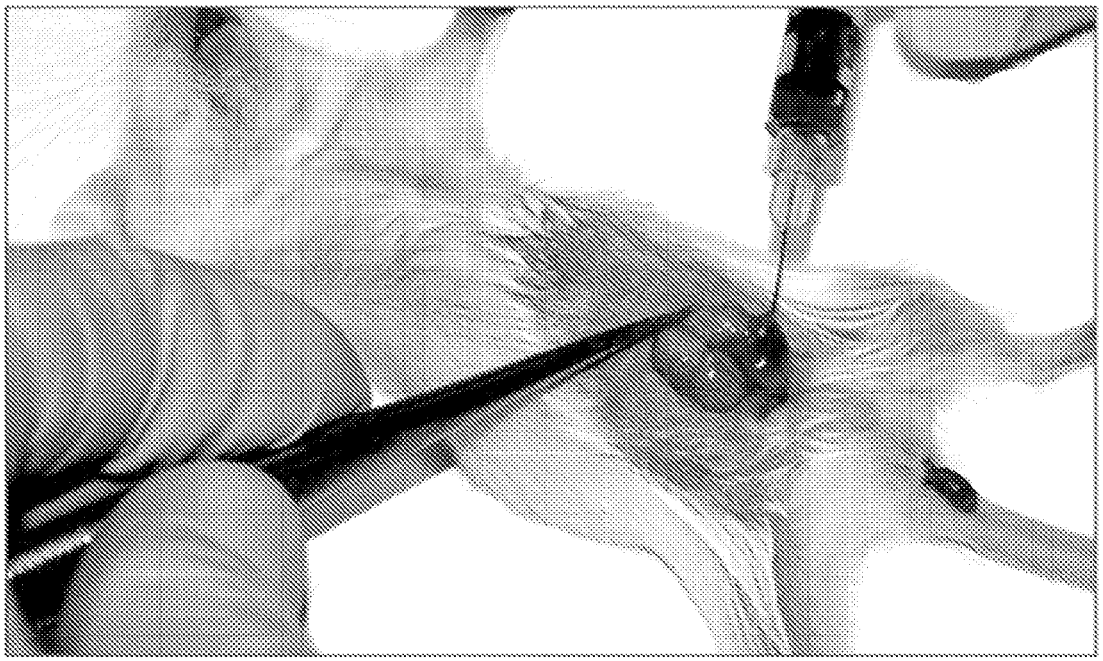
Figure 1:
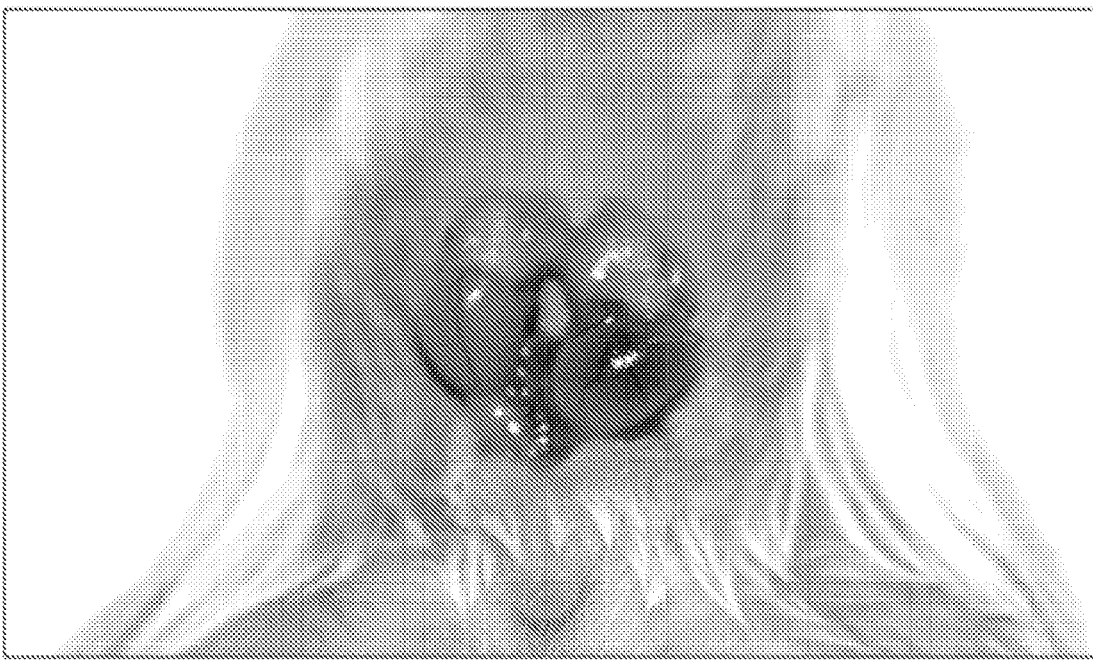
Figure 1:
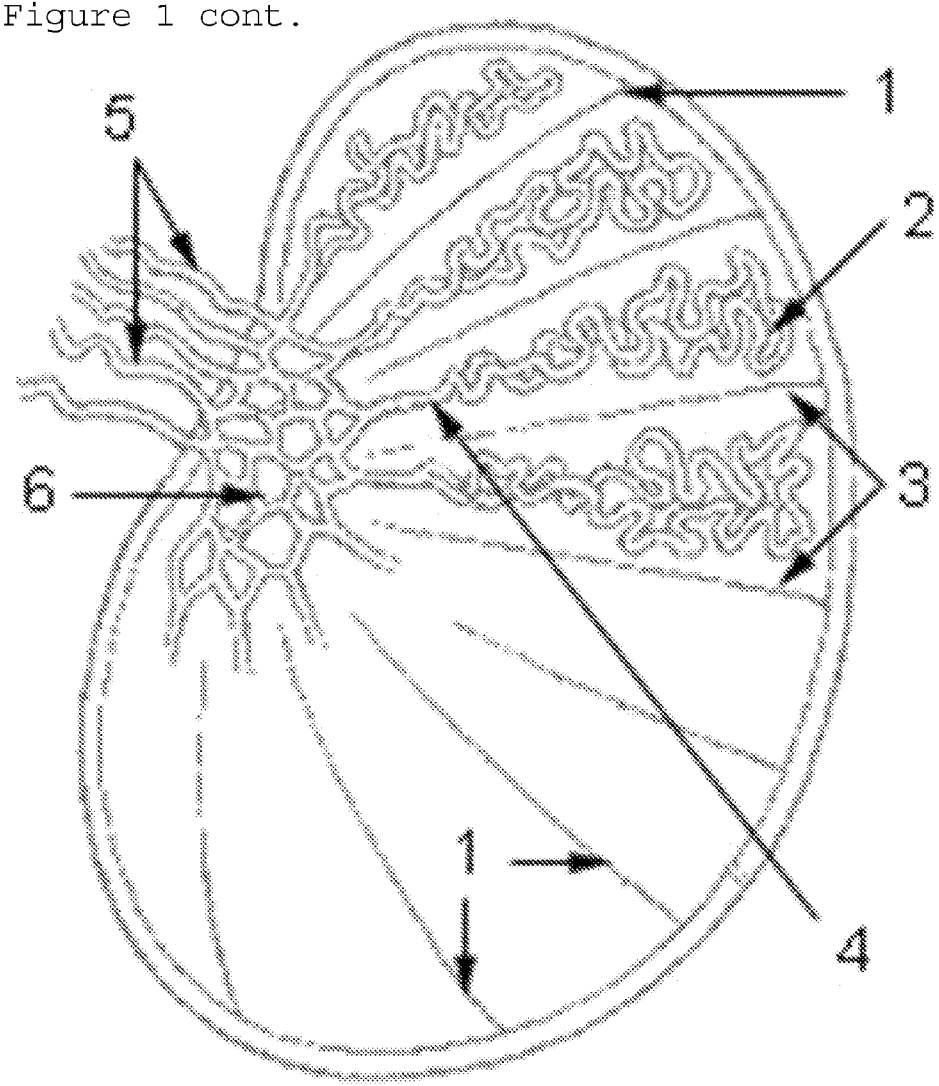

1: Testicular septa
2: Convoluted seminiferous tubules
3: Testicular lobules
4: Straight seminiferous tubules
5: Efferent ductules
6: Rete testis

PROCESS FOR GENERATING TRANSGENIC ANIMALS USING RECOMBINANT LENTIVIRUSES

CROSS-REFERENCE TO RELATED APPLICATIONS

This application claims priority to Indian Application No. 2442/DEL/2010 filed on Oct. 13, 2010, which is incorporated herein by reference in their entireties.

FIELD OF INVENTION

This invention relates to a process for generation transgenic animals using recombinant lentiviruses.

BACKGROUND OF THE INVENTION

The generation of genetically modified animals has spurred great advances in our understanding of various aspects of growth and development. Multiple technologies have used either injection into a two celled embryo followed by implantation into a pseudo pregnant mother, or using stem cell aggregation techniques to generate either knockout or knockdown mice. These experiments are expensive, labor-intensive, time-consuming and require several female mice to serve as donors for embryos and to serve as pseudo pregnant mothers for transplantation with a number of invasive surgical procedures.

Spermatogonial stem cells are responsible for the production of spermatozoa by spermatogenesis[4] and hence an appropriate target for the germline modification. Earlier groups have generated transgenic mice by spermatogonial stem cell manipulation in vitro using either recombinant retroviruses or lentiviruses to infect spermatogonial stem cells in vitro and then transplant the cells into the testes of isogenic adult male mice, however, in some cases the recipient mice were unreceptive to the donor spermatogonial cells. Additionally, a loss of fertility has also been observed in some mice after in vivo transfection of testicular germ cells with retroviral constructs carrying a Iacz gene, and only 26% of the fertile males sired transgenic mice contributing to a poor success rate of 2.8%. In vitro manipulation of spermatogonial cells using lentiviral vectors followed by micro injection in testis increased the success rate to 6%. Recently, Majumdar and colleagues have generated transgenic mice by electroporation of an expression construct into the testes of adult male mice. While most of the fore founder mice were able to sire transgenic pups, the percentage of pups that were transgene positive is not known. Further, it was not clear whether germline transmission of the transgene was achieved.

All prior experiments involved manipulation of the spermatogonial cells in vitro followed by implantation into a donor. This is not a very efficient process and thus results in a low number of progeny that express the transgene in question. In practice this means that it sometimes takes one or two years to develop a transgenic mouse model which often retards scientific progress. While electroporation of DNA into the testes of the male mouse has avoided a number of these problems, the currently available data do not indicate whether the transgene is transmitted in the germ line. Therefore, there is a need for new technologies for generating transgenic mice that will address the issues raised above.

OBJECTS OF THE INVENTION

An object of this invention is to propose a rapid process for generating a transgenic animal such as a mouse;

Another object of this invention is to propose a process which will allow the generation of knockdown mice that lack gene function;

Still another object of this invention is to propose a process that can be used to generate a conditional knockdown of specific gene products that can be controlled in a temporal and tissue specific fashion;

Further, object of this invention is to propose new cost effective, faster technique with a high success rate for generation of transgenic mice by in vivo viral transduction of the gene of interest into undifferentiated spermatogonial stem cells.

BRIEF DESCRIPTION OF THE INVENTION

According to this invention there is provided A process for generating transgenic animals using recombinant lentiviruses comprising the steps of:

injecting recombinant lentivirus into the interstituim of the testis of a male mouse to produce spermatozoa expressing the transgene with a span of 30-35 days, subjecting the male mice with expressing lentivirus to the step of mated with wild type female mouse determining whether the progeny from the said cross carried the transgene.

BRIEF DESCRIPTION OF THE ACCOMPANYING DRAWINGS

FIG. 1: Injection of virus into seminiferous tubules. The intertubular spaces of anesthetized mice were injected with a virus solution containing trypan blue to mark the injected testes as shown in the top two panels. The third panel shows a diagram of the testes with different regions from the testes indicated. As in clear from the slide, anything injected into the intertubular spaces will reach the seminiferous tubules resulting in infection of spermatogonial stem cells.

Figure 2:
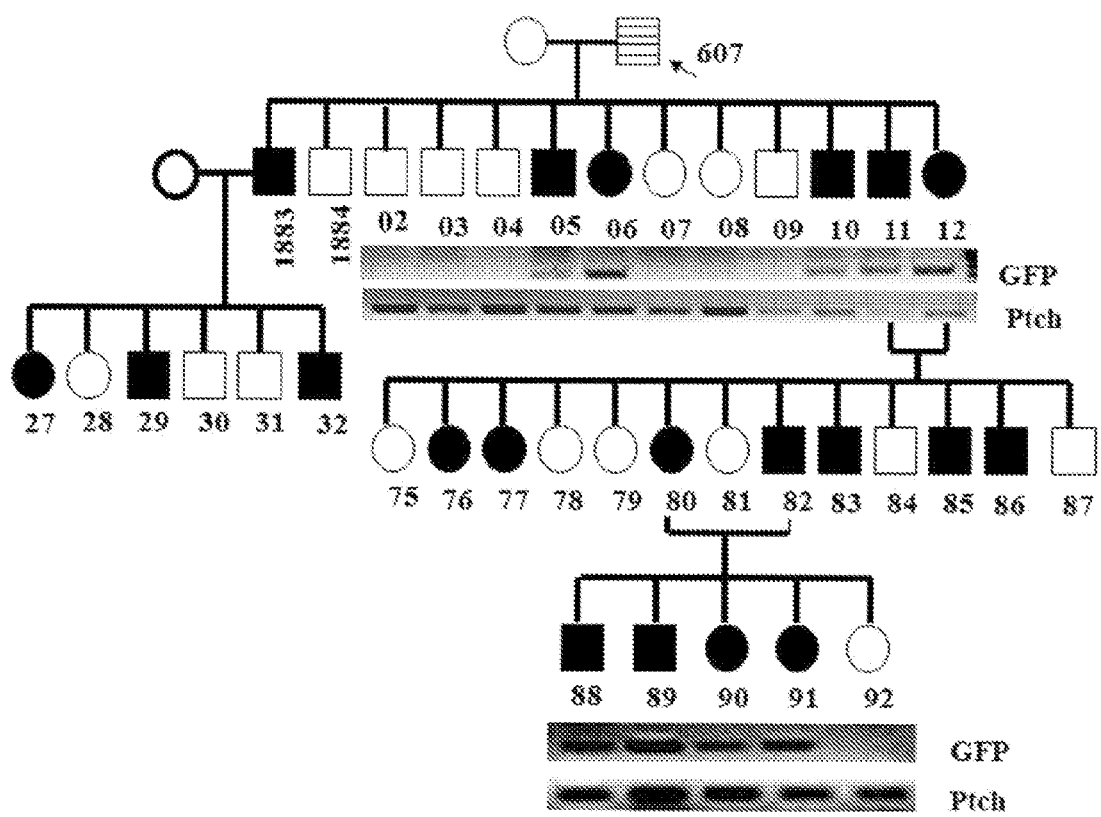
Figure 2:
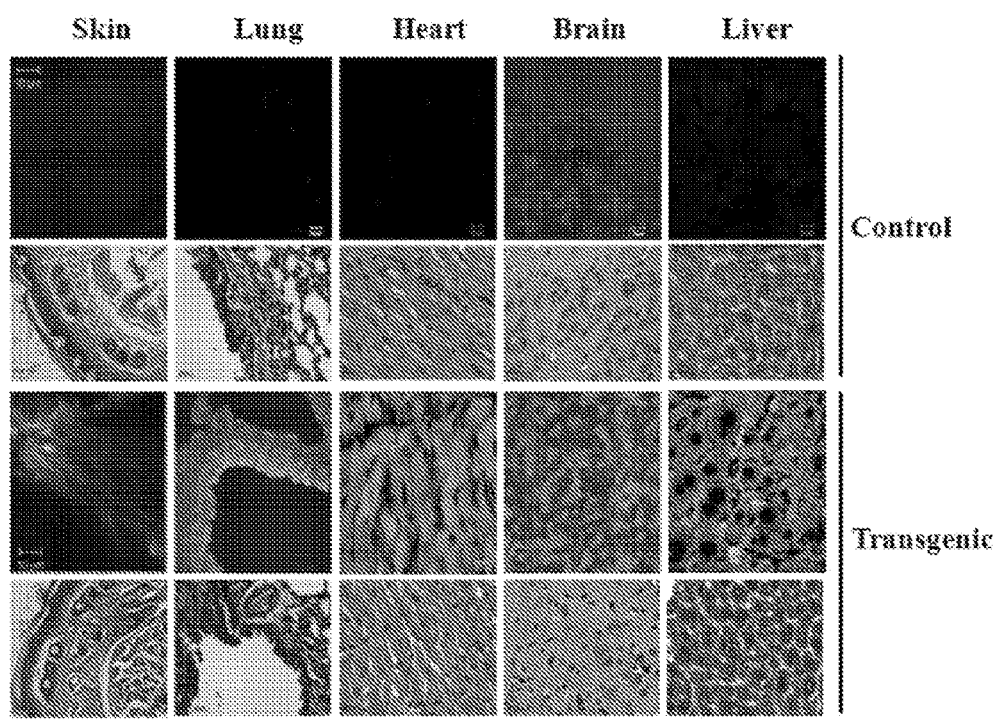

FIG. 2: Generation of transgenic mice. A. The hatched box illustrates the founder animal. White and black circles are transgene negative and transgene positive females respectively while white and black boxes are transgene negative and transgene positive males respectively. Panels show ethidium bromide staining of gels showing amplification of the transgene from genomic DNA. An amplification for the patch gene was performed to serve as a loading control. B. Tissue sections from the transgene positive (transgenic) or transgene negative mice (control) were examined for the presence of the EGFP-f protein by fluorescence microscopy or stained with hematoxylin and eosin to denote tissue morphology. Note the high fluorescent signal from the transgenic mouse as compared to the control.

DETAILED DESCRIPTION OF THE INVENTION

The present invention relates to the process has refined the existing process of making transgenic animals to the point where a rate of positive progeny is over 60%. This is almost ten fold higher than the rates obtained with previous technology and will enhance the ability of scientists, who are interested in developing animal models for disease processes, to develop mouse models for research. This process will revolutionize the generation of transgenic animals for biomedical research. Further, we believe that this technique could be easily adapted using current technology to other animal species resulting in the generation of multiple genetically modified animals for research and for industrial purposes.

The generation of genetically modified animals has spurred great advances in our understanding our various aspects of growth and development. Multiple technologies have used either injection into a two celled embryo followed by implantation into a pseudo pregnant mother, or using stem cell aggregation techniques to generate either knockout or knockdown mice. These experiments are expensive, labor-intensive, time-consuming and require several female mice to serve as donors for embryos and to serve as pseudo pregnant mothers for transplantation with a number of invasive surgical procedures.

Spermatogonial stem cells are responsible for the production of spermatozoa by spermatogenesis and hence an appropriate target for germline modification. Earlier groups have generated transgenic mice by spermatogonial stem cell manipulation in vitro using either recombinant retroviruses or lentiviruses to infect spermatogonial stem cells in vitro and then transplant the cells into the testes of isogenic adult male mice, however, in some cases the recipient mice were unreceptive to the donor spermatogonial cells. Additionally, a loss of fertility has also been observed in some mice after in vivo transduction of testicular germ cells with retroviral constructs carrying a lacZ gene, and only 26% of the fertile males sired transgenic mice contributing to a poor success rate of 2.8%. In vitro manipulation of spermatogonial cells using recombinant lentiviruses followed by micro-injection in testis increased the success rate to 6%. Recently, Majumdar and colleagues have generated transgenic mice by electroporation of an expression construct into the testes of adult male mice. While most of the fore founder mice were able to sire transgenic pups, the percentage of pups that were transgene positive is not known. Further, it was not clear whether germline transmission of the transgene was achieved. However, in other studies where the transgene was introduced in the testis by in vivo electroporation, either the expression did not last long or the transgene was not integrated in the germline and was found to be dominantly expressed in sertoli cells.

The prior experiments involved manipulation of the spermatogonial cells in vitro followed by implantation into a donor. This is not a very efficient process and thus results in a low number of progeny that express the transgene in question. In practice this means that it sometimes takes one or two years to develop a transgenic mouse model which often retards scientific progress. While electroporation of DNA into the testes of the male mouse has avoided a number of these problems, current data do not indicate whether the transgene is transmitted in the germ line. Therefore, there is a need for new technologies for generating transgenic mice that will address the issues raised above. Our method bypasses the need for implantation by injecting lentiviruses directly into the testes resulting in increased transgene integration into spermatogonial stem cells. The use of recombinant lentiviruses ensures that even cells that are not actively dividing are infected and that the transgene integrates into the cells genomic DNA allowing for inheritance of the transgene in the germline. This allows the rapid generation of transgenic animals with minimal invasive procedures and is cost effective, ethical and does not require expensive infrastructure.

New cost effective, faster technique with a high success rate for generation of transgenic mice by in vivo viral transduction of the gene of interest into undifferentiated spermatogonia. Recombinant lentiviruses expressing EGFP-f were injected into the intertubular spaces of the testis targeting undifferentiated spermatogonia present in the seminiferous tubules (FIG. 1). The intertubular spaces allows the lentivirus to infect undifferentiated spermatogonial cells located at the basement of the seminiferous tubules.

5-10 µl of EGFP recombinant EGFP-f lentivirus ($5.8 \times 10^6$ TU/ml) was injected into the interstituim of the testis of a 28 days old Crl:CFW(SW) male mouse. The undifferentiated spermatogonial cells in mice produce mature spermatozoa in 35 days. Hence, mice infected with EGFP-f expressing lentivirus were mated with wild type females of the same strain after 35 days. These male mice were referred as pre-founder because they were used to generate founder mice. To determine whether the progeny from this cross carried the transgene, the EGFP-f transgene was amplified from genomic DNA isolated from the animals. An amplification for the patch gene served as an internal control (FIG. 2A). Six out of thirteen pups were found to be positive for the presence of the EGFP-f transgene suggesting that the lentivirus is able to mediate transgenesis by in vivo infection of spermatogonial cells (FIG. 2A). To further validate the procedure of in-vivo infection we independently replicated the process with two additional male pre-founder mice. Similar results were observed (Table 1). A summary of the generation of the initial founder mice is shown in Table 1 which shows that 61% of the progeny from the first cross are transgene positive. This is much higher than previously reported rates and illustrates the efficiency of the procedure used. To determine whether the transgene is inheritable and if the fertility of the founder mice is compromised, founder mice 11 and 12 were interbred to generate additional transgenic animals. Seven of the thirteen pups from this cross contained the transgene (FIG. 2A). When two pups from this cross were inbred, almost all the mice showed the presence of the transgene suggesting that the inheritance of the transgene was stable. Further, another transgene positive mouse, 1883, was out-bred with a wild type female mouse of the same strain. Three of the six pups from this cross showed the presence of the transgene (FIG. 2A). To determine whether the transgene was expressed in multiple tissues, tissue sections from organs of F1 or F2 mice were analyzed for the presence of the EGFP-F transgene by fluorescence microscopy. As shown in FIG. 2B, sections from the transgenic mice showed green fluorescence in multiple tissues, when compared to the control mice. We are now in the process of developing knockout mice that have expression of specific gene products using the same technology.

TABLE 1

A summary for the generation of the initial founder mice from three independent male pre-founder mice.

| Pre-founder mouse | Founder mice per litter | Founder mice per litter positive for EGFP-f |
|---|---|---|
| 607 | 8 | 1 |
| 607 | 11 | 9 |
| 607 | 6 | 4 |
| Total | 25 | 14 |
| Success rate | | 56% |
| 608 | 8 | 5 |
| 608 | 6 | 4 |
| 608 | 8 | 4 |
| Total | 22 | 13 |
| Success rate | | 59% |
| 609 | 8 | 4 |
| 609 | 12 | 10 |
| 609 | 13 | 7 |
| Total | 33 | 22 |
| Success rate | | 66% |
| Grand Total | 80 | 49 |
| Cumulative success rate | | 61.25% |

We claim:

1. A process of generating a non-human transgenic animal comprising the steps of:
    injecting a recombinant lentivirus comprising a transgene operatively linked to a promoter into the space between the seminiferous tubules of a testis of a non-human male, thereby transducing a spermatozoa present in said testis of said non-human male with said transgene, wherein said transgene incorporates into the genome of said spermatozoa;
    mating the non-human male with a non-human female to produce progeny; and
    identifying the progeny comprising the transgene, thereby producing a non-human transgenic animal.

2. The process as claimed in claim 1, wherein said transgene encodes a GFP-f.

3. The process as claimed in claim 1, wherein 5-10 μl of said recombinant lentiviruses is injected.

4. The process as claimed in claim 1, wherein said non-human male is a 28 day old male mouse at the time of said injecting said recombinant lentivirus.

5. The process as claimed in claim 1, wherein injecting said recombinant lentivirus and transducing said spermatozoa produces spermatozoa expressing said transgene within 35 days.

6. The process as claimed in claim 1, wherein 61% of the progeny are transgene positive.

* * * * *